United States Patent [19]

Masters

[11] Patent Number: 5,201,715
[45] Date of Patent: Apr. 13, 1993

[54] IMPLANTABLE DEVICES HAVING ULTRASONIC ECHOGRAPHIC SIGNATURE

[75] Inventor: Martin Masters, Santa Barbara, Calif.

[73] Assignee: McGhan Medical Corporation, Santa Barbara, Calif.

[21] Appl. No.: 797,115

[22] Filed: Nov. 19, 1991

[51] Int. Cl.$^5$ ............................................. A61M 5/00
[52] U.S. Cl. ................... 604/175; 128/662.03
[58] Field of Search ............... 604/175, 93; 128/660.07, 662.03, 915, 916

[56] References Cited

U.S. PATENT DOCUMENTS

| | | | |
|---|---|---|---|
| 3,919,724 | 11/1975 | Sanders et al. | 604/175 |
| 4,341,120 | 7/1982 | Anderson | 128/916 |
| 4,633,883 | 1/1987 | Matsui | 128/660.07 |
| 4,697,595 | 10/1987 | Breyer et al. | 128/660.07 |
| 4,710,174 | 12/1987 | Moden et al. | 604/175 |
| 4,760,837 | 8/1988 | Petit | 604/175 |
| 4,781,680 | 11/1988 | Redmond et al. | 604/93 |
| 4,781,685 | 11/1988 | Lehmann et al. | 604/175 |
| 4,785,818 | 11/1988 | Hardin | 128/660.07 |
| 4,861,341 | 8/1989 | Woodburn | 604/175 |
| 4,862,892 | 9/1989 | Green | 128/660.07 |
| 4,932,414 | 6/1990 | Coleman et al. | 128/662.03 |
| 5,042,493 | 8/1991 | Saito et al. | 128/662.03 |

Primary Examiner—Paul J. Hirsch
Attorney, Agent, or Firm—Michael G. Petit

[57] ABSTRACT

A target having a characteristic ultrasonic signature for implantation beneath the skin is described. The target, when placed within an implanted injection port enables ultrasonic echographic discrimination of the target from surrounding tissue. In particular, the target enables one to locate its position beneath the skin non-invasively by means of ultrasonic echograpy. In practice, the signature comprises reflections of ultrasonic waves from a target comprising varying thicknesses of a material having sound transmission characteristics different from human tissue. Ultrasonic sound waves reflected from different surfaces of the target arrive at a detector with a characteristic time delay thereby providing a signature. Biocompatible plastics, such as methacrylate, polysulfone, polytetrafluoroethylene or polyethylene, or elastomers such as silicone may be used for the target.

5 Claims, 4 Drawing Sheets

IMPLANTABLE DEVICES HAVING ULTRASONIC ECHOGRAPHIC SIGNATURE

BACKGROUND OF THE INVENTION

1. Field of the Invention

The present invention is directed to a target for the ultrasonic location of an article implanted beneath the skin.

2. Brief Description of the Prior Art

Objects for implantation beneath the skin are well known in the art. Among such articles for implantations are tissue expander devices. Such tissue expander devices are implanted beneath the skin thereafter to be inflated to stretch the overlying tissue to prepare, for example, a skin flap for grafting. More commonly, tissue expander devices are implanted beneath the skin and slowly inflated to create a pocket into which a prosthetic device may be permanently placed, such as a mammary implant. Such tissue expander devices require slow inflation. This is accomplished by the co-implantation of an injection port with a fill reservoir connected to the interior of the tissue expander. Some prior art fill ports are domed to enable their location beneath the skin by means of palpation. Once located, the fill port reservoir is accessed by means of the transdermal placement of a needle into a self-sealing septum on the injection port. The subsequent injection of fluid into the port inflates the expander device. Since it is necessary to pierce the septum (which septum is self-sealing to the track of a needle when the needle is removed), it is fundamental that means for accurately locating the septum beneath the skin are available.

To enable the facile location of deeply implanted injection ports, Sampson, et al., U.S. Pat. No. 4,222,374, describe a device for locating the septum of the injection port by means of a magnetic indicator. Sampson's septum locating apparatus comprises means mounted in an implantable device for producing an energy pattern that emanates from the patient's body. The pattern is shaped so as to "target" the device's septum that underlies the patient's skin. In one embodiment of the invention the energy pattern-producing means is one or more permanent magnets which are shaped and/or arranged relative to the septum so as to generate a magnetic field pattern external to the patient's body which indicates the septum's location.

In general, Sampson teaches the placement within the "target" of a radiation source; the radiation source of preference being a magnet. Other radiation sources might include radioactive elements. The only constraint being that the energy pattern production means comprises one or more sources of corpuscular radiation mounted in the implant device in juxtaposition with its septum so that the radiation pattern emanating from the patient's body provides an indication of the septum location.

Sampson, et al., in their preferred embodiment, include a small hand held detector that is responsive to the magnetic energy pattern produced by the septum designating source incorporated into the implanted device. When the detector is moved along the patient's body over or adjacent to the general vicinity of the implanted device, the detector responds to the energy pattern by the motion of a gimbled bar magnet thereby producing a visible indication of the location of the septum relative to the detector. Thus, following these indications the physician manipulating the detector can steer the detector until a reticule on the detector directly overlies the implanted septum. Then using the reticule as an aiming point, the physician can mark the patient's skin and be assured that the implanted septum is located directly underneath that mark.

There are two problems associated with the use of magnets in juxtaposition to the septum. The first is that most such magnetic materials capable of generating a magnetic field are radiopaque. Thus, tumors and the like adjacent to a radiopaque radiation source would not be apparent under x-ray. Increasingly, whole body nuclear magnetic resonance spectroscopy (NMR) is gaining favor in diagnostic laboratories. The NMR diagnostic technique requires the use of magnetic fields penetrating the body. The accuracy of NMR depends upon the magnetic field strength at a particular point in the body. The external field imposed by the nuclear magnetic resonance device can be altered locally by the presence of the magnet within an injection port rendering diagnostic imaging of tissues close to the magnet by NMR difficult, if not impossible. Further, if an implanted target should have its integrity breached, the release of ferromagnetic material or the exposure of the body to ferromagnetic material comprising the target might have deleterious results. For these reasons it is desirable to have a non-magnetic target. It would be further desirable to have a targeting signature which is easily distinguished from surrounding tissue yet is not radiopaque.

SUMMARY OF THE INVENTION

Accordingly, it is an object of the present invention to provide an implantable target having a characteristic ultrasonic signature.

Yet another object of the invention is to provide an ultrasonically locatable septum for implantation beneath the skin which is self-contained and requires no external power supply.

Another object is to provide a target for implantation providing a distinguishable ultrasonic signature which target is radiolucent.

Another object is to provide a target for implantation beneath the skin which provides a characteristic ultrasonic echographic signature enabling the precise location of a target-bearing device implanted within the body by ultrasonic means.

Yet another object of the invention is to provide a target which is relatively inexpensive to make and requires minimum maintenance.

Yet another object of this invention is to provide a target having ultrasonic signature which is bio-compatible.

It is still another object of this invention to provide a target which is non-radiative.

Other objects of the invention will become apparent as we turn to the drawings and description of the preferred embodiments.

BRIEF DESCRIPTION OF THE DRAWINGS

For a fuller understanding of the nature and objects of the invention reference should be made to the following detailed description taken in connection with the accompanying drawings which are.

FIGS. 3a-3f show the detection of the reflected ultrasonic signals on an oscilloscope screen.

FIGS. 4 a-d shows cross-sectional views of four additional embodiments of targets having characteristic ultrasonic signatures.

FIGS. 5 a-h show cross-sectional views of various septums having a distinctive ultrasonic signature.

DESCRIPTION OF THE PREFERRED EMBODIMENTS

Generally, in pulse-echo ultrasound imaging of a target the system design assumes the propagation of acoustic pulses through a homogeneous tissue medium with a uniform velocity of sound usually taken to be 1540 m/sec. This assumption is used, for example, in converting round trip pulse- echo time of flight into target range. Unfortunately, this simplest model is not valid. The body is actually composed of inhomogeneous layers of differing tissues with bumps and ridges of varying thicknesses and acoustic velocities. These layers may intervene between the transducer and the target of interest. The propagation velocity of ultrasound varies from approximately 1470 m/sec in fat to greater than 1600 m/sec in muscle and nervous tissue to as much as 3700 m/sec in bone. Such variations in the speed of sound in the tissues can result in multiple reflections and loss of image quality. Nevertheless, if the target is relatively close to the surface of the skin with fairly homogeneous intervening tissue, the ultrasonic echographic image quality is in most cases sharp enough for accurate detection.

Figure 1:
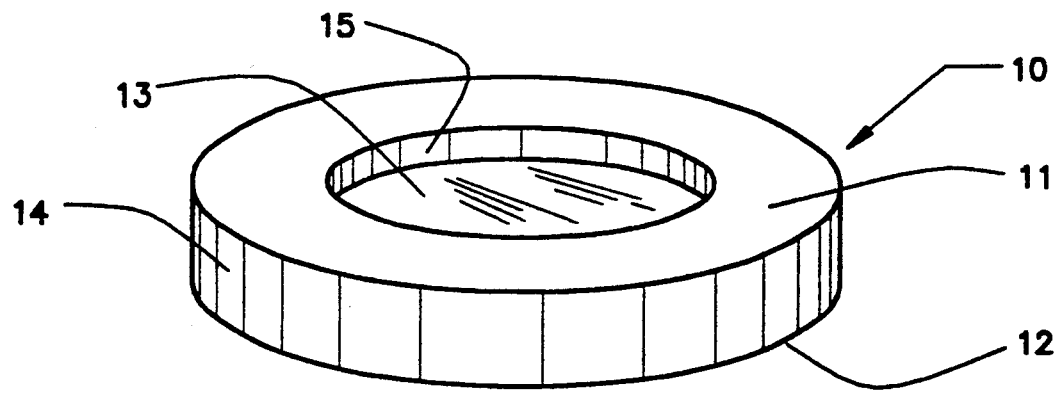
FIG. 1 is a perspective view of a first preferred embodiment of an ultrasonic targeting device.

Turning now to FIG. 1, we see a target suitable for implantation beneath the skin in juxtaposition to a septum of a injection reservoir. The target, generally indicated at 10, comprises a disc-shaped section of plastic having an outer wall 14, an upper surface 11, and a lower surface 12, upper and lower surfaces being substantially planar and parallel to one another. A recessed annular center characterized by a second planar surface 13 parallel to the planes of the parallel upper surface 11 and the lower surface 12, and delineated by an annular wall 15, is also present. Such a target may be conveniently made from methalmethacrylate or silicone although any material that is bio-compatible and has a sound velocity significantly different from the surrounding tissue is suitable.

Figure 2:
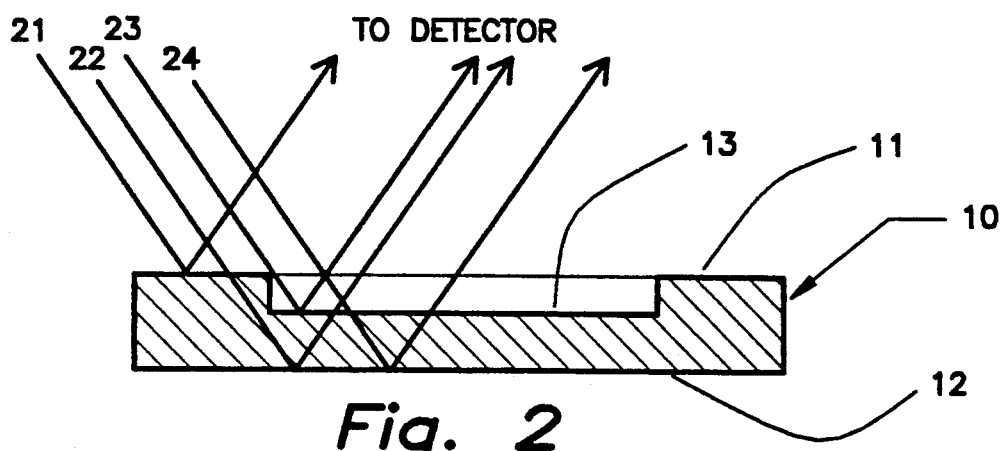
FIG. 2 is a cross sectional view of the first preferred embodiment of an ultrasonic targeting device of FIG. 1 showing reflections of ultrasonic waves from various surfaces of the target.

In FIG. 2 an ultrasonic source irradiates the target and multiple reflections occur from the surfaces thereof. Sound wave 21 is reflected from the upper surface 11 of the target. Ultrasonic wave 22 is reflected from the lower surface 12 of the target while ultrasonic wave 23 is reflected from the inner surface 13 of the target and the ultrasonic wave 24 is reflected from the lower surface 12 of the target. Of course, the signals reflected from the target will be strongest when the target and the detector ar the closest together. That is to say, when the detector is directly over the target.

Figure 3A:
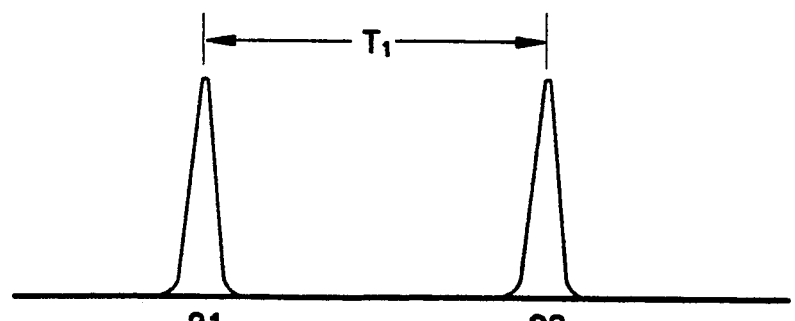

Turning now to FIG. 3 we see in FIG. 3a the detected reflection from ultrasonic wave 21, designated 21 on FIG. 3a, and after a time lag T1 we see the arriving pulse 22 from ultrasound wave 22 reflected from the bottom of the target. The time difference is T1.

Figure 3B:
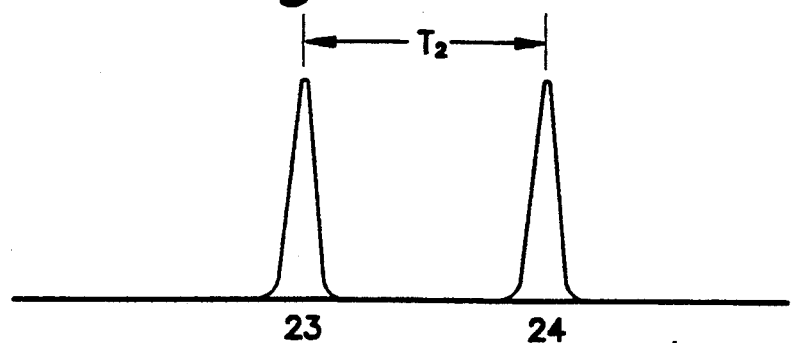
Figure 4A:
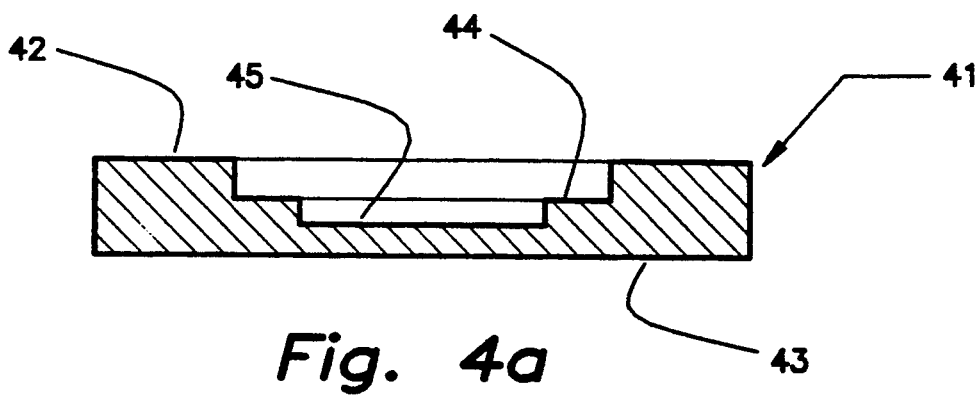
Figure 4B:
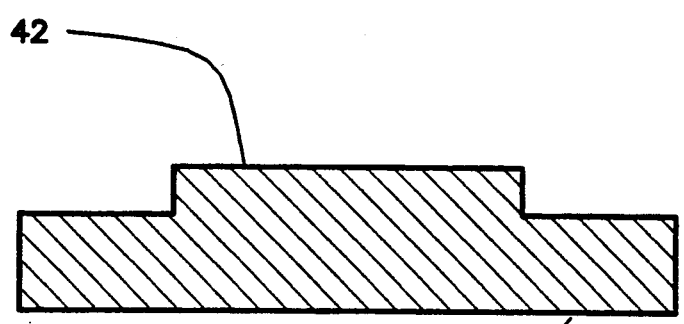
Figure 4C:
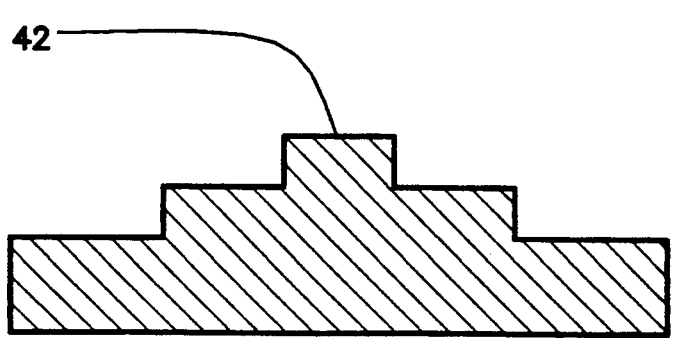
Figure 4D:
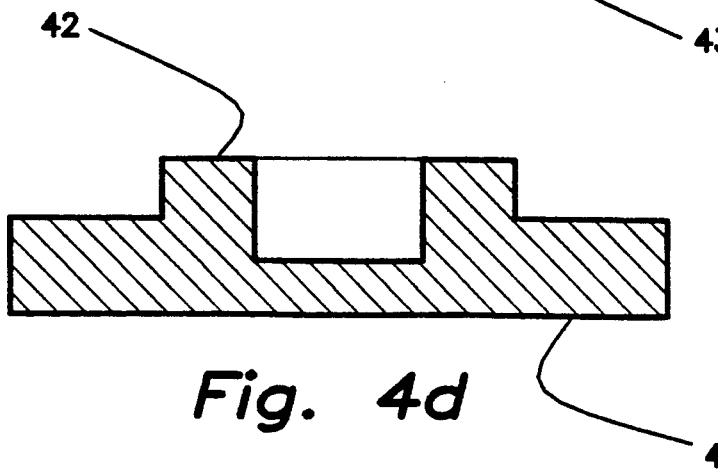

Turning now to FIG. 3b, we see that ultrasonic wave 23, since it travels further than 21 has been right shifted by a small amount relative to the reflection from the bottom of the target 24 and the delay now has been changed to T2. Thus, by scanning over the surface of the skin with a pulsed ultrasonic source of a type well known in the art of echographic detection and location and described below, and an ultrasonic detector, when the detector is directly overlying the target 10, we will either observe two relatively strong pulses separated by time interval T1, or two pulses separated by time interval T2. If T1 is observed, then the device is not directly over the center of the target. In practice slight oscillatory motion of the ultrasonic detector may be performed until the time difference T2 is observed. Then the position of the detector should be marked as directly over the target.

Additional embodiments of an implantable target having distinguishable ultrasonic signatures are shown in FIG. 4. FIG. 4a is a cross-sectional view of a disc-shaped target 41 having an upper surface 42, a lower surface 43 and two intermediate annular, parallel surfaces 44 and 45. The time delay of the ultrasonic pulse echoes (not shown) from the various layers provide a distinctive and characteristic signature for this target. Similar targets are shown in cross-sectional view in FIGS. 4b-d. All of the targets have upper 42 and lower 43 reflective parallel surfaces with one or more planar coparallel surfaces interposed therebetween. The foregoing targets all describe an integral target structure. It is also possible to form a ultrasonically reflective target by laminating together sheets of biocompatible materials having different ultrasonic reflectivities to produce a reflective target signature resembling a bar code.

Devices for the exploration of media by ultrasonic echography, or an ultrasonic echograph, comprises in general at least one ultrasonic transducer associated on the one hand with a stage for the emission of the ultrasonic waves towards the target embedded in the tissue and, on the other hand, with a stage for the reception and/or for the processing of the ultrasonic echoes returned by the various reflective surfaces encountered by the ultrasonic waves within the tissue. Such echograph devices are well known in the art. (See for example U.S. Pat. No. 5,010,885 to Fink, et al., issued Apr. 30, 1991). The use of and of the targets described herein with such an echograph is useful for obtaining the objects of this invention.

The above-described targets are particularly useful for finding an injection port implanted beneath the skin of a patient. Since such injection ports move around beneath the skin following implantation such a simple device as tattooing the overlying skin following implantation is of little use for locating the injection port a month or two thereafter. If, however, a target having a characteristic ultrasonic pulse echographic signal such as has been described herein is placed within the injection port so as to underlie the septum, the position of the septum can be readily determined by ultrasonic means. Once the position of the target beneath the skin has been determined a needle may be introduced through the skin to penetrate the septum of the injection port. The placement of the needle may alternatively be verified within the injection port by a needle placement verifier such as that described in U.S. Pat. No. 4,760,837 to Petit, or U.S. Pat. No. 5,009,644 to McDonald.

Figure 5A:
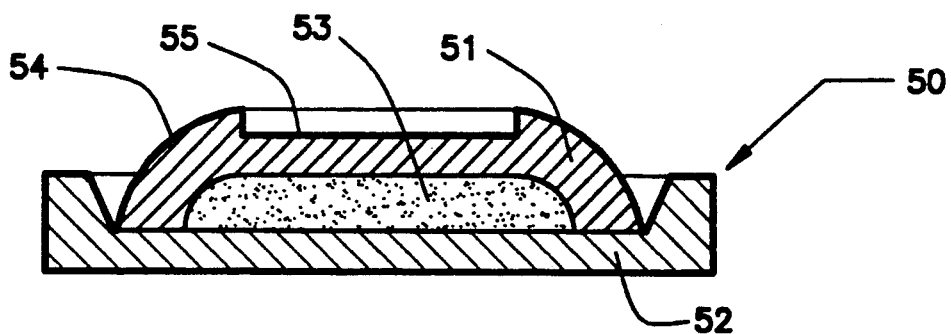
Figure 5B:
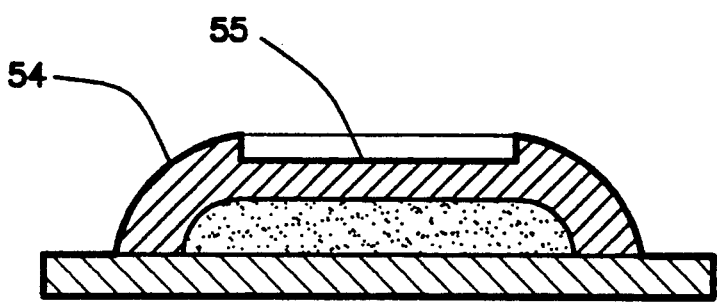
Figure 5C:
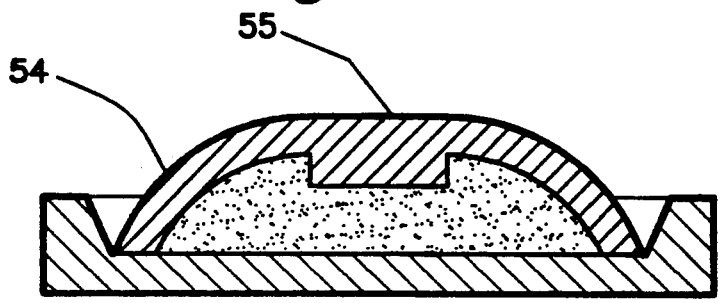
Figure 5D:
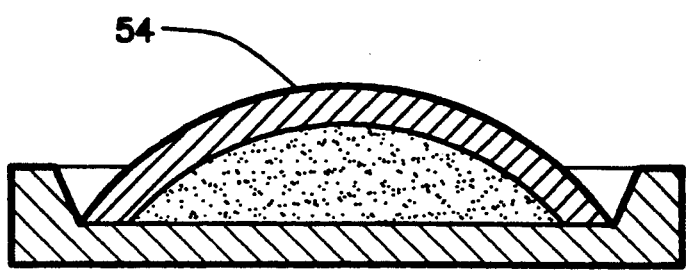
Figure 5E:
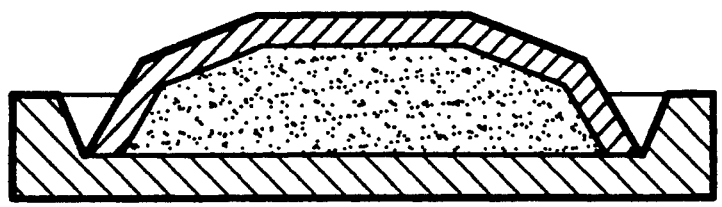
Figure 5F:
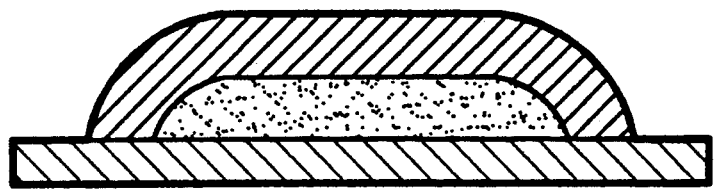
Figure 5G:
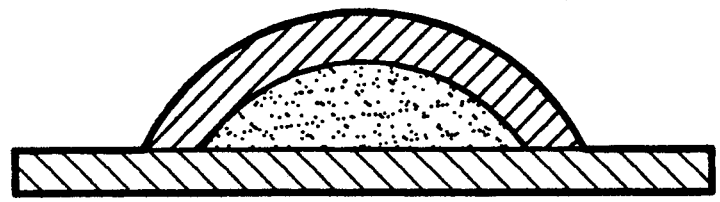
Figure 5H:
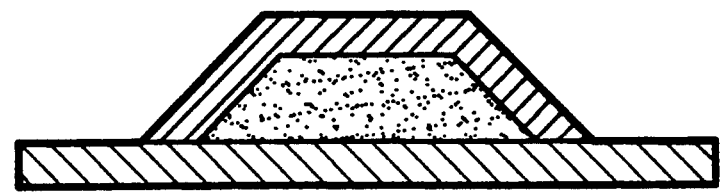

It is possible and, in many instances, even preferable to fabricate the septum of an injection port to have an ultrasonic echographic signature. That is, the septum is the target. Examples of various embodiments of such septums giving rise to a characteristic ultrasonic echographic signature are shown in FIGS. 5 a-h. A typical injection port or generally indicated at numeral 50, is shown in cross-section in FIG. 5a. The injection port 50 comprises a self-sealing septum 51 through which a hollow bore needle (not shown) may be inserted, a needle guard 52 prevents the tip of the needle so inserted from progressing beyond the boundary of the reservoir 53. The reservoir 53 is normally in fluid communication with an implantable device such as a catheter or tissue expander (not shown) by means of a conduit (not shown). The advantage of a septum having both a curved portion 54 and an apical flat portion 55 is that as an ultrasonic source (not shown) is moved toward the septum it will receive a relatively weak reflected signal from opposing faces of the curved portion 54 which increase in amplitude as the ultrasonic source/detector approaches the septum. When the ultrasonic source/detector directly overlies the septum, it receives a new signature from reflection from both opposing surfaces of the apical flat portion 55 which may be either thicker (FIGS. 5c and 5f) or thinner (FIGS. 5a and 5b) than the curved portion 54 of the septum. A septum having a characteristic ultrasonic signature made from silicone with the shape shown in FIGS. 5a and 5b is a particularly preferred embodiment. In this embodiment the septum 51 comprises a domed, hemispherical silicone member with curved sides 54 and a flat apex 55. The thickness of the wall of the septum 51 is preferably different in the curved portion 54 than in the flat portion 55. The reflected ultrasonic signal (not shown) from the curved portion 54 enables a searcher to move toward the septum while the relatively strong reflected signal from opposing faces of the flat portion 55 indicate the detector is directly over the center of the septum.

Numerous alternative embodiments can be made which depend upon the difference in the time of travel of ultrasound from an upper surface to one or more lower surfaces of the target device. A detector may be designed so that the time difference between arriving signals can trigger an audible signal which changes in frequency with the time delay between returning pulses. While the invention is illustrated in terms of several integral unitary targets comprising a bio-compatible plastic having two or more planar surfaces parallel to one another, it is understood by those skilled in the art that one can practice the invention with other obvious embodiments. The examples given here is intended only for teaching the invention. The scope of the invention is set forth in the claims appended hereto.

What I claim is:

1. A device for implantation beneath the skin thereafter to be located by non-invasive ultrasonic means, said device having a target affixed thereto, said target comprising a biocampatible material having a plurality of ultrasonically reflective surfaces, said plurality of ultrasonically reflective surfaces, in combination, providing a characteristic ultrasonic echographic signature.

2. The device of claim 1 wherein said biocompatible material has an acoustical velocity which is different from the acoustical velocity of human tissue.

3. The device of claim 1 wherein said target further comprises a laminate structure consisting of substantially planar layers of biocompatible materials bonded together.

4. The device of claim 2 wherein said target is a unitary structure.

5. A septum for an implantable fill port comprising a generally dome-shaped elastomer member having an apex, said member being self sealing to the track of a hollow bore needle and said apex having an ultrasonic echographic signature characteristic of the apex of the member.

* * * * *